(12) United States Patent
Sue et al.

(10) Patent No.: US 11,574,140 B2
(45) Date of Patent: Feb. 7, 2023

(54) SYSTEMS AND METHODS TO PROCESS ELECTRONIC IMAGES TO DETERMINE SALIENT INFORMATION IN DIGITAL PATHOLOGY

(71) Applicant: PAIGE.AI, Inc., New York, NY (US)

(72) Inventors: Jillian Sue, New York, NY (US); Thomas Fuchs, New York, NY (US); Christopher Kanan, Rochester, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/313,617

(22) Filed: May 6, 2021

(65) Prior Publication Data

US 2021/0350166 A1    Nov. 11, 2021

Related U.S. Application Data

(60) Provisional application No. 63/021,955, filed on May 8, 2020.

(51) Int. Cl.
*G16H 30/20* (2018.01)
*G16H 50/20* (2018.01)
(Continued)

(52) U.S. Cl.
CPC ........... *G06K 9/623* (2013.01); *G06K 9/6256* (2013.01); *G06T 7/0012* (2013.01); *G16H 30/20* (2018.01);
(Continued)

(58) Field of Classification Search
CPC combination set(s) only.
See application file for complete search history.

(56) References Cited

U.S. PATENT DOCUMENTS 5,261,406 A * 11/1993 MacKay ............. A61B 6/4258
600/407
7,244,230 B2 * 7/2007 Duggirala ............... A61B 8/56
600/443
(Continued)

FOREIGN PATENT DOCUMENTS

WO    2019084697 A1    5/2019

OTHER PUBLICATIONS

Markus D. Herrmann et al "Implementing the DICOM Standard for Digital Pathology" (Year: 2018).*
(Continued)

*Primary Examiner* — Tsung Yin Tsai
(74) *Attorney, Agent, or Firm* — Bookoff McAndrews, PLLC (57) ABSTRACT

Systems and methods are disclosed for identifying a diagnostic feature of a digitized pathology image, including receiving one or more digitized images of a pathology specimen, and medical metadata comprising at least one of image metadata, specimen metadata, clinical information, and/or patient information, applying a machine learning model to predict a plurality of relevant diagnostic features based on medical metadata, the machine learning model having been developed using an archive of processed images and prospective patient data, and determining at least one relevant diagnostic feature of the relevant diagnostic features for output to a display.

17 Claims, 7 Drawing Sheets

(51) Int. Cl.
*G06K 9/62* (2022.01)
*G06T 7/00* (2017.01)

(52) U.S. Cl.
CPC ... *G16H 50/20* (2018.01); *G06T 2207/20076* (2013.01); *G06T 2207/20081* (2013.01); *G06T 2207/20104* (2013.01); *G06T 2207/30024* (2013.01); *G06V 2201/03* (2022.01)

(56) References Cited

U.S. PATENT DOCUMENTS

| | | | | |
|---|---|---|---|---|
| 7,664,604 | B1* | 2/2010 | Heine | G16H 50/50 |
| | | | | 702/19 |
| 9,779,213 | B2* | 10/2017 | Donovan | G16H 50/50 |
| 2002/0188196 | A1* | 12/2002 | Burbank | A61B 8/481 |
| | | | | 600/431 |
| 2004/0147840 | A1* | 7/2004 | Duggirala | G06T 7/0012 |
| | | | | 600/437 |
| 2005/0010445 | A1* | 1/2005 | Krishnan | G16H 50/20 |
| | | | | 706/45 |
| 2010/0184093 | A1* | 7/2010 | Donovan | G16H 50/50 |
| | | | | 435/287.1 |
| 2011/0176710 | A1* | 7/2011 | Mattiuzzi | G06T 7/0012 |
| | | | | 382/128 |
| 2013/0080134 | A1* | 3/2013 | Donovan | G16Z 99/00 |
| | | | | 703/11 |
| 2015/0072371 | A1 | 3/2015 | Marugame | |
| 2019/0206056 | A1 | 7/2019 | Georgescu et al. | |
| 2019/0392944 | A1* | 12/2019 | Samset | G16H 30/40 |
| 2020/0129155 | A1* | 4/2020 | Elgena | A61B 8/5207 |
| 2021/0350166 | A1* | 11/2021 | Sue | G06K 9/6256 |

OTHER PUBLICATIONS

Kaustav Bera et al "Artificial intelligence in digital pathology—new tools for diagnosis and precision oncology" (Year: 2019).*
Sérgio Francisco da Silva et al. "Improving the ranking quality of medical image retrieval using a genetic feature selection method" (Year: 2011).*
Dmitriy Zinovev et al. "Predicting Radiological Panel Opinions Using a Panel of Machine Learning Classifiers " (Year: 2009).*
International Search Report and Written Opinion dated Aug. 9, 2021 in counterpart International Patent Application No. PCT/US2021/031068 (13 pages, in English).

* cited by examiner

SYSTEMS AND METHODS TO PROCESS ELECTRONIC IMAGES TO DETERMINE SALIENT INFORMATION IN DIGITAL PATHOLOGY

RELATED APPLICATION(S)

This application claims priority to U.S. Provisional Application No. 63/021,955 filed May 8, 2020, the entire disclosure of which is hereby incorporated herein by reference in its entirety.

FIELD OF THE DISCLOSURE

Various embodiments of the present disclosure pertain generally to image-based feature identification and related image processing methods. More specifically, particular embodiments of the present disclosure relate to systems and methods for identifying diagnostic features based on processing images of tissue specimens.

BACKGROUND

Pathology is a visual discipline that includes specialized interpretation of morphological and histological patterns. Whole slide images (WSI) of pathology specimens consist of hundreds of thousands of pixels that a pathologist must review. Although not all of the pixels contain relevant information, pathologists may need to review the entire WSI before rendering a diagnosis. The present disclosure describes visualizations that allow pathologists to focus their attention on relevant region(s) for a quick, complete, and correct diagnosis.

According to one or more embodiments in the present disclosure, outputs may be leveraged from systems developed to identify specific features on whole slide images of pathology tissue, saving pathologists time by targeting their attention to areas on the whole slide image that are relevant for a specific question, or for the diagnosis.

Additionally, the present disclosure describes additional methods for visualizing identified cancerous foci of interest on whole slide images of digitized pathology images (e.g., other than heatmaps over all identified regions of interest).

SUMMARY

According to certain aspects of the present disclosure, systems and methods are disclosed for identifying a diagnostic feature of a digitized pathology image.

A method for identifying a diagnostic feature of a digitized pathology image, the method including: receiving one or more digitized images of a pathology specimen, and medical metadata comprising at least one of image metadata, specimen metadata, clinical information, and/or patient information; applying a machine learning model to predict a plurality of relevant diagnostic features based on medical metadata, the machine learning model having been developed using an archive of processed images and prospective patient data; and determining at least one relevant diagnostic feature of the relevant diagnostic features for output to a display.

A system for identifying a diagnostic feature of a digitized pathology image includes a memory storing instructions; and at least one processor executing the instructions to perform a process including receiving one or more digitized images of a pathology specimen, and medical metadata comprising at least one of image metadata, specimen metadata, clinical information, and/or patient information; applying a machine learning model to predict a plurality of relevant diagnostic features based on medical metadata, the machine learning model having been developed using an archive of processed images and prospective patient data; and determining at least one relevant diagnostic feature of the relevant diagnostic features for output to a display.

A non-transitory computer-readable medium storing instructions that, when executed by a processor, cause the processor to perform a method for identifying a diagnostic feature of a digitized pathology image, the method including receiving one or more digitized images of a pathology specimen, and medical metadata comprising at least one of image metadata, specimen metadata, clinical information, and/or patient information; applying a machine learning model to predict a plurality of relevant diagnostic features based on medical metadata, the machine learning model having been developed using an archive of processed images and prospective patient data; and determining at least one relevant diagnostic feature of the relevant diagnostic features for output to a display.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Identifying areas of interest is a time-intensive process, which includes visual interpretation by specialists. As the number of pathologists decreases across the world, the volume of pathological specimens for review are increasing, which causes physician burnout and misdiagnoses.

The process of analyzing an entire WSI for all slides in a patient case may be entirely manual, which is extremely time-consuming and error prone. Regions of interest may include features that are a fraction of the entire tissue (e.g., micrometers in size). At academic medical centers, pathologists in training (e.g., fellows) will manually review patient's cases in advance of the pathologist's review. During review, the fellows will mark areas of interest and pre-write a diagnosis for the pathologist's final review and diagnosis. In this method, pathologists are drawn to specific parts of the cases based on the trainee's initial assessment. If pathologists are unsure of the final and/or differential diagnosis, they have the option to send the material to a different pathologist for a second opinion. The referral pathologist may only be sent the representative slide(s) for the specific question—in this scenario, the pathologist's attention is focused to a specific question and foci.

The present disclosure uses artificial intelligence (AI) technology that detects features of interests (e.g., biomarkers, cancer, histological, etc.) that may be used for pathological diagnosis and treatment decisions. This may be done at the case, part, block levels, and/or slide levels. Data and predictions are aggregated and made available instantaneously via any user interface (e.g., through a digital pathology viewing system, report, or laboratory information system, etc.).

Figure 1A:
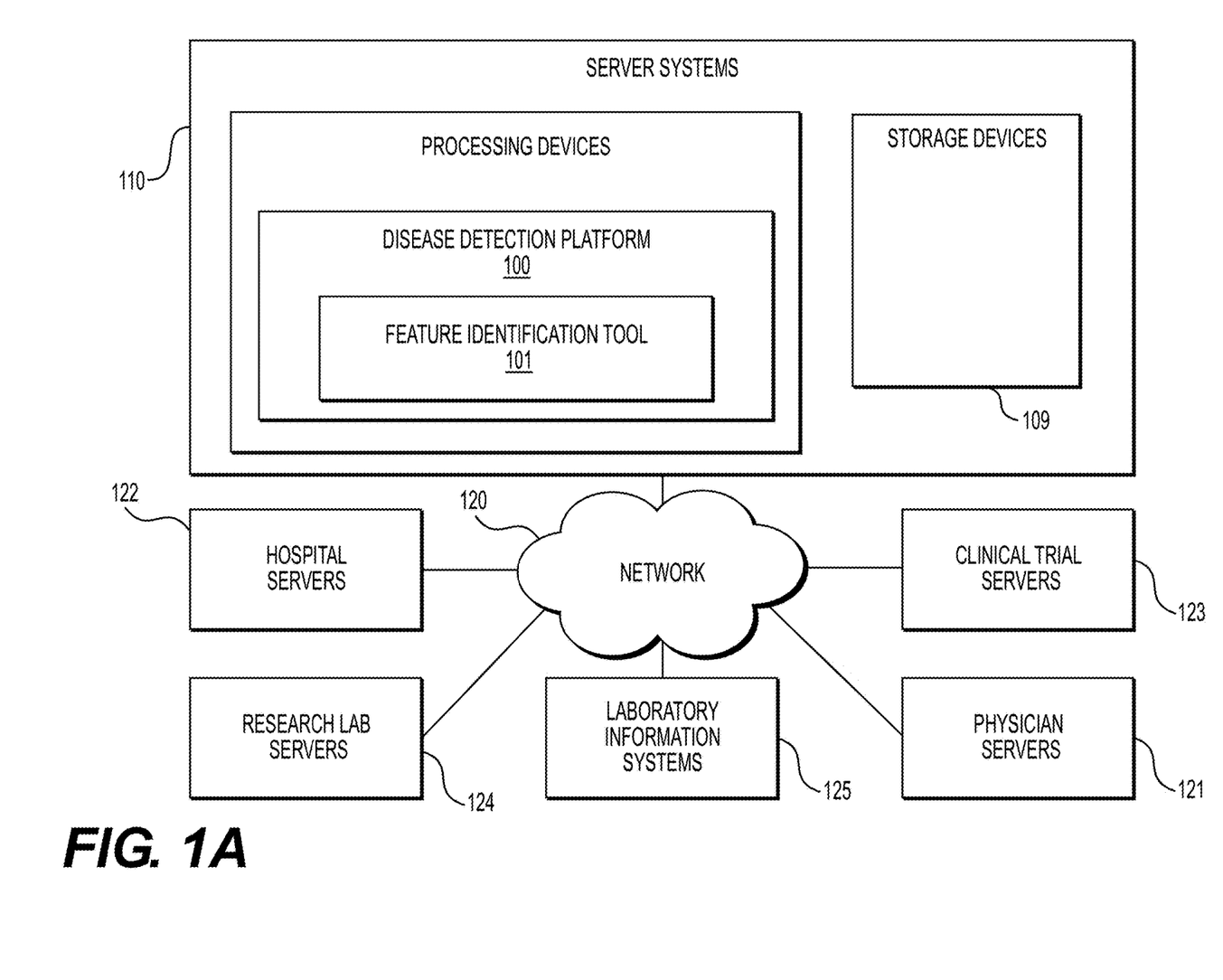
FIG. 1A illustrates an exemplary block diagram of a system and network for identifying diagnostic features of an image, according to an exemplary embodiment of the present disclosure.

FIG. 1A illustrates an exemplary block diagram of a system and network for identifying diagnostic features of an image, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a feature identification tool 101 for identifying diagnostic features pertaining to digital pathology image(s), and using machine learning to identify the diagnostic features, according to an exemplary embodiment of the present disclosure. Exemplary machine learning models may include, but are not limited to, any one or any combination of Neural Networks, Convolutional neural networks, Random Forest, Logistic Regression, and/or Nearest Neighbor.

The physician servers 121, hospital servers 122, clinical trial servers 123, research lab servers 124, and/or laboratory information systems 125 may create or otherwise obtain images of one or more patients' cytology specimen(s), oncology specimen(s), slide(s) of the cytology/oncology specimen(s), digitized images of the slide(s) of the cytology/oncology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and laboratory information systems 125 refer to systems used by pathologists for reviewing the images of the slides. In hospital settings, tissue type information may be stored in a laboratory information system 125.

Figure 1B:
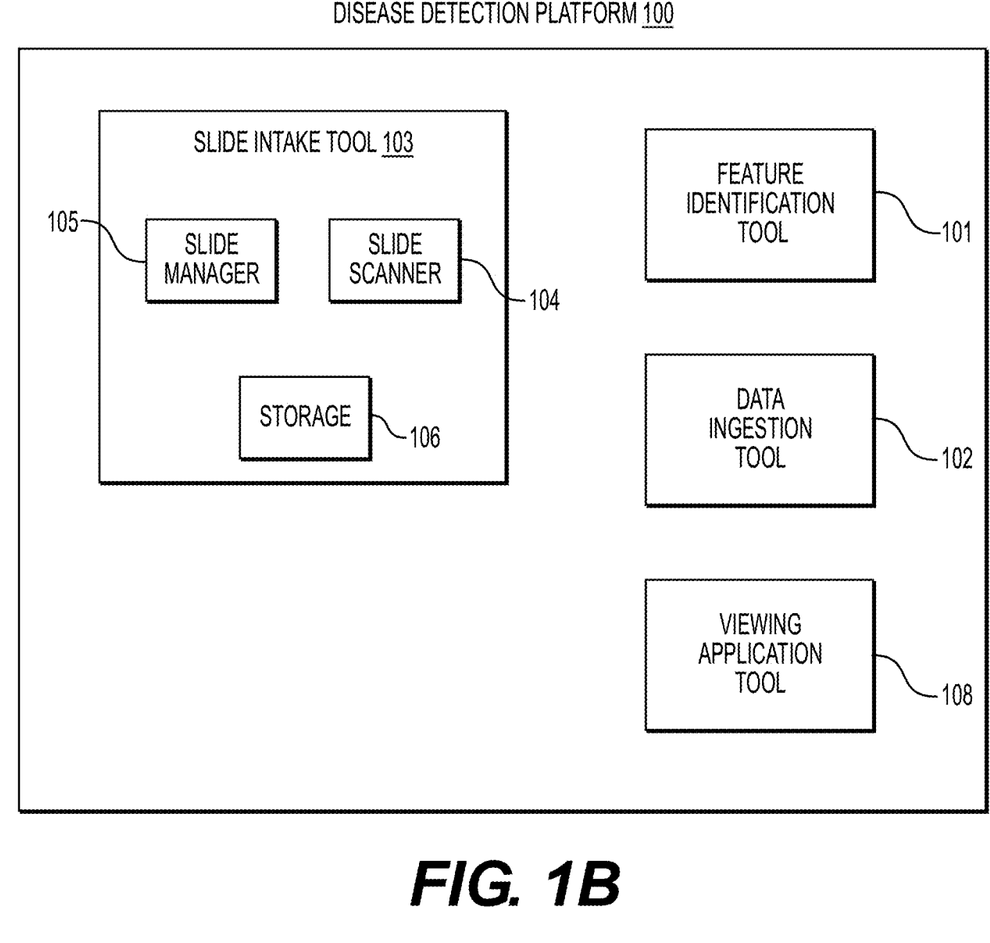
FIG. 1B illustrates an exemplary block diagram of the disease detection platform 100, according to an exemplary embodiment of the present disclosure.

FIG. 1B illustrates an exemplary block diagram of a disease detection platform 100 for identifying diagnostic features pertaining to digital pathology image(s), using machine learning.

Specifically, FIG. 1B depicts components of the disease detection platform 100, according to one embodiment. For example, the disease detection platform 100 may include a feature identification tool 101, a data ingestion tool 102, a slide intake tool 103, a slide scanner 104, a slide manager 105, a storage 106, and a viewing application tool 108.

The feature identification tool 101, as described below, refers to a process and system for identifying diagnostic features pertaining to digital pathology image(s), and using machine learning to identify the diagnostic features, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in a storage, such as storage 106 and/or storage devices 109.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The feature identification tool 101, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include storage devices for storing images and data received from at least one of the feature identification tool 101, the data ingestion tool 102, the slide intake tool 103, the slide scanner 104, the slide manager 105, and/or viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 2:
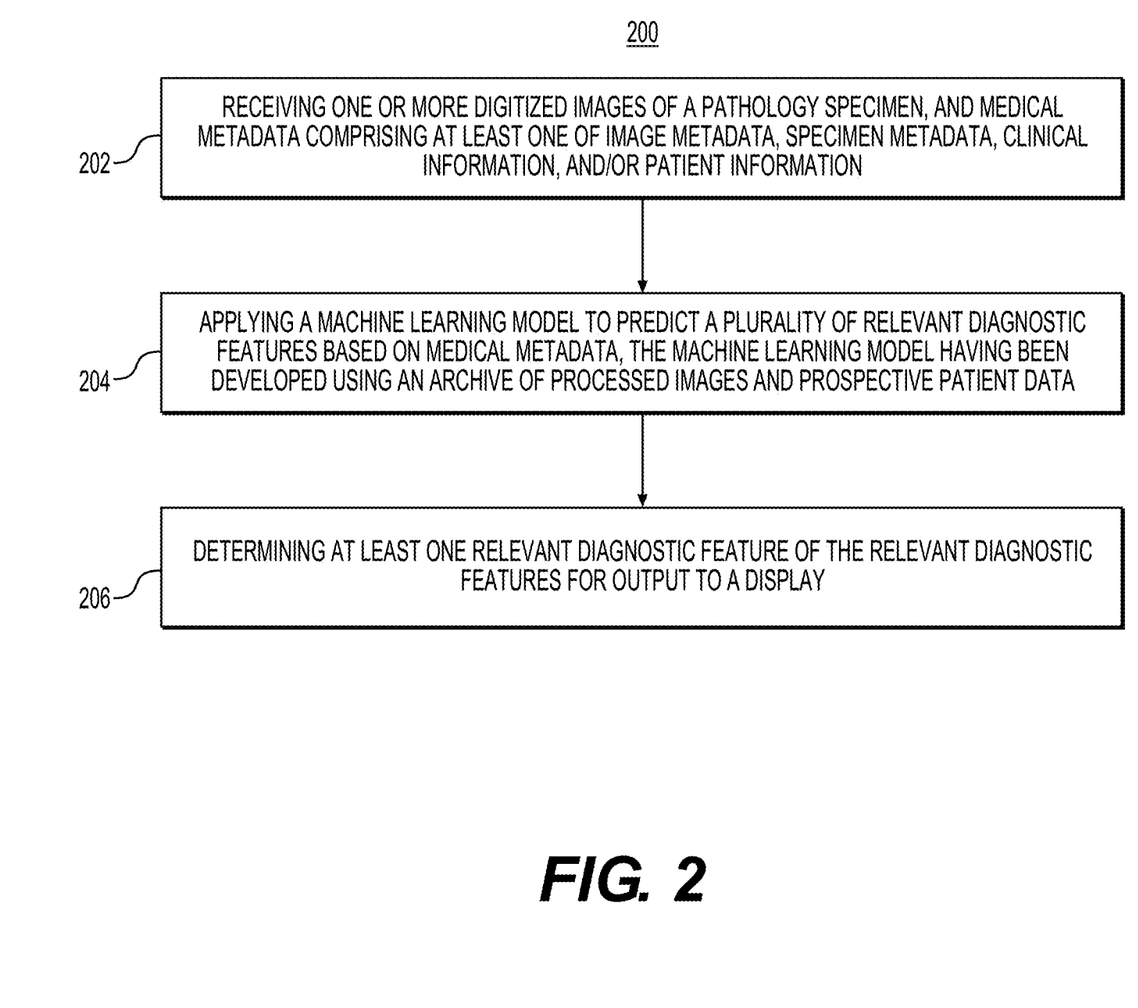
FIG. 2 is a flowchart of an exemplary method for developing a feature identification tool, according to an exemplary embodiment of the present disclosure.

FIG. 2 is a flowchart illustrating an exemplary method of developing a tool for identifying a diagnostic feature of a digitized pathology image, according to an exemplary embodiment of the present disclosure. For example, an exemplary method 200 (e.g., steps 202 to 206) may be performed by the feature identification tool 101 automatically or in response to a request from a user (e.g., pathologist, patient, oncologist, etc.).

Exemplary Feature Identification Tool Development: An exemplary method 200 for developing a feature identification tool may include one or more of the steps below. In step 202, the method may include receiving one or more digitized images of a pathology specimen (e.g., histology), and medical metadata comprising at least one of image metadata, specimen metadata (e.g., specimen type, available parts, gross description, etc.), clinical information (e.g., diagnosis, biomarker information, lab results, etc.), and/or patient information (e.g., demographics, gender, etc.). The method may include developing a pipeline that archives processed images and prospective patient data. Additionally, data may be stored into a digital storage device (e.g., hard drive, network drive, cloud storage, RAM, etc.). In step 204, the method may include applying a machine learning model to predict a plurality of relevant diagnostic features based on medical metadata, the machine learning model having been developed using an archive of processed images and prospective patient data (e.g., tissue type, specimen type, stain type, pathologist, etc.). In step 206, the method may include determining at least one relevant diagnostic feature of the relevant diagnostic features for output to a display. Prediction results may be converted into a visual output depending on a type of user (e.g., pathologist, patient, oncologist, etc.), and the results may be displayed in a format based on the type of user and the use case (e.g., interactive, structured, templatized, static, etc.).

Figure 3:
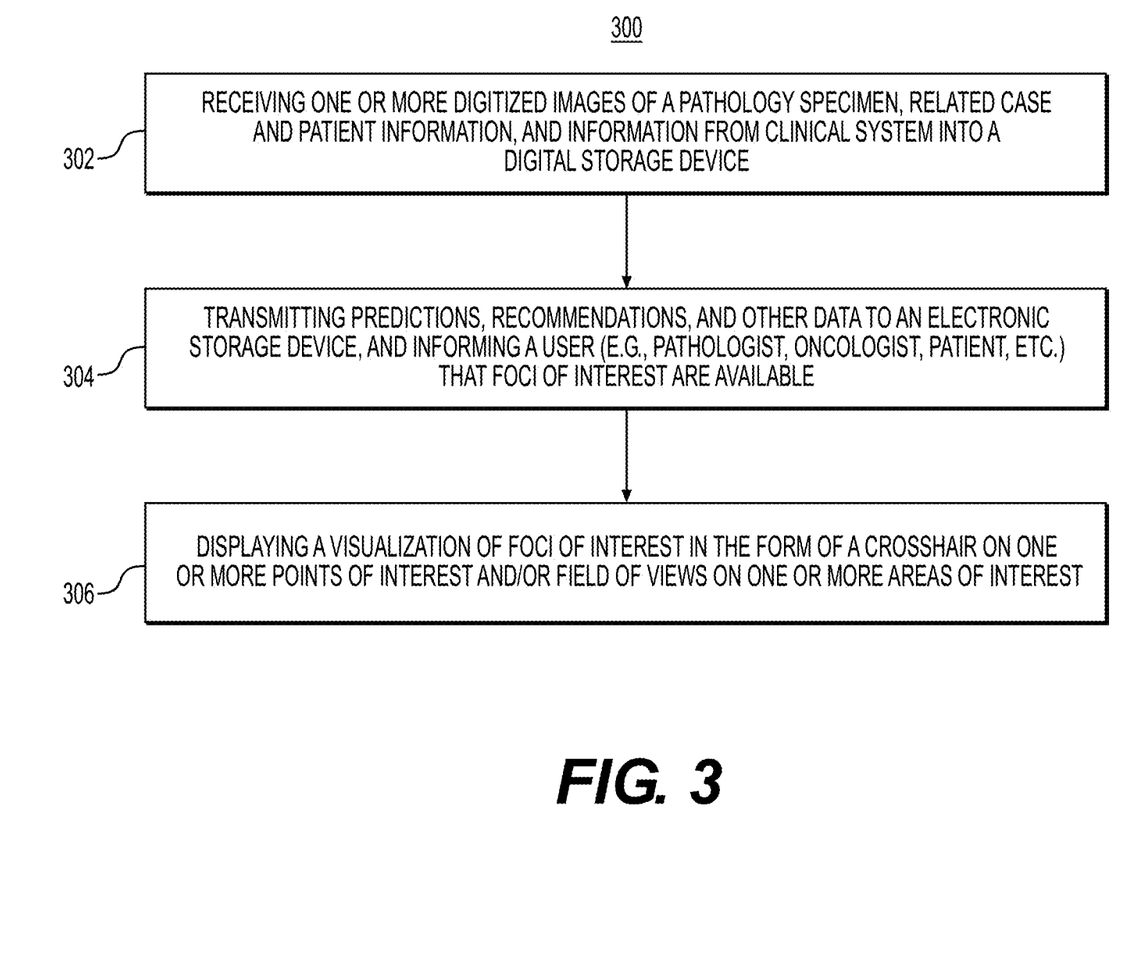
FIG. 3 is a flowchart of an exemplary method for developing a feature identification tool, according to an exemplary embodiment of the present disclosure.

FIG. 3 is a flowchart illustrating an exemplary method of using a tool for identifying a diagnostic feature of a digitized pathology image, according to an exemplary embodiment of the present disclosure. For example, an exemplary method 300 (e.g., steps 302 to 306) may be performed by the feature identification tool 101 automatically or in response to a request from a user (e.g., pathologist, patient, oncologist, etc.).

Figure 4:
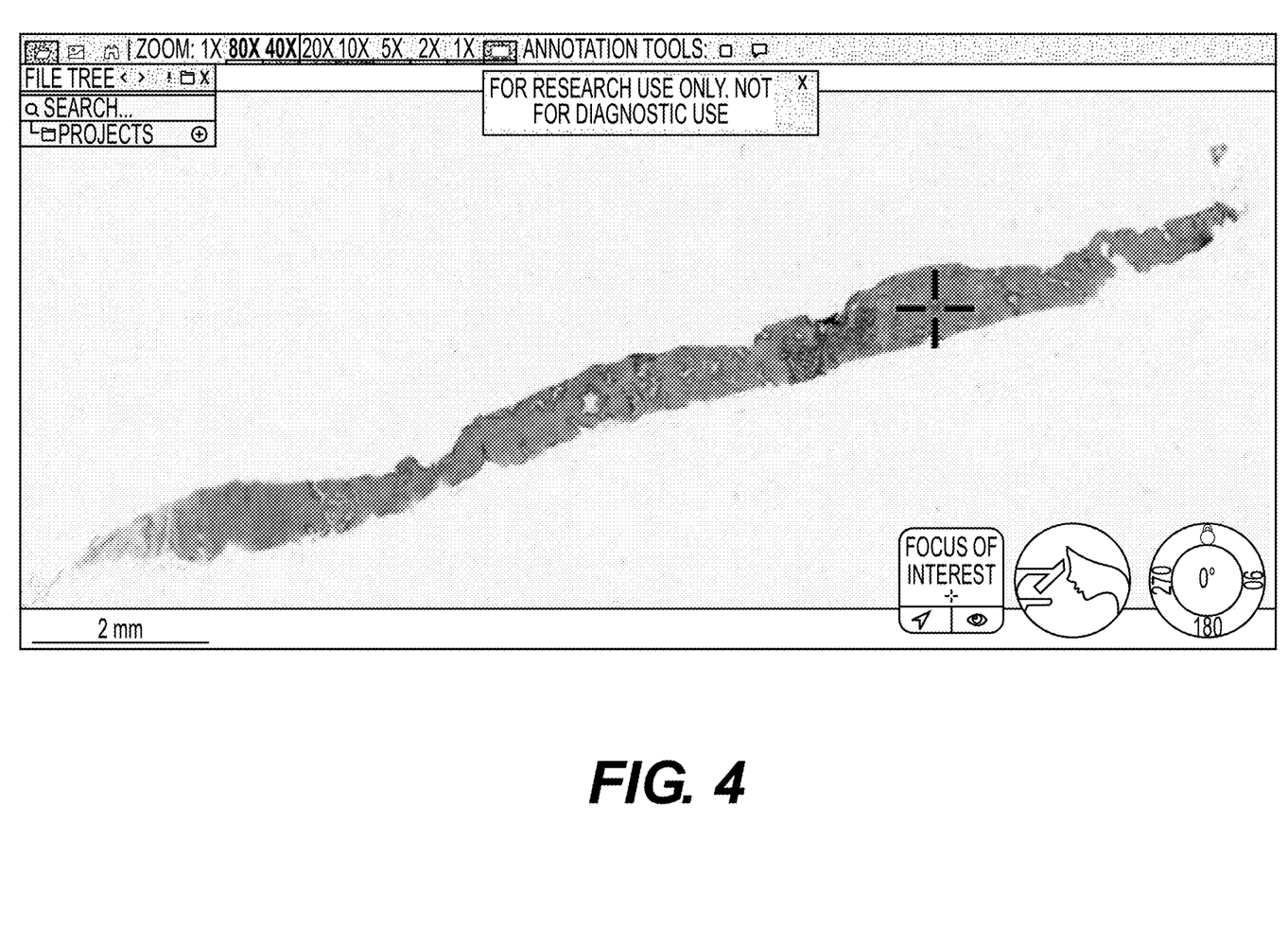
FIG. 4 is a diagram illustrating an example crosshair output, according to an exemplary embodiment of the present disclosure.
Figure 5:
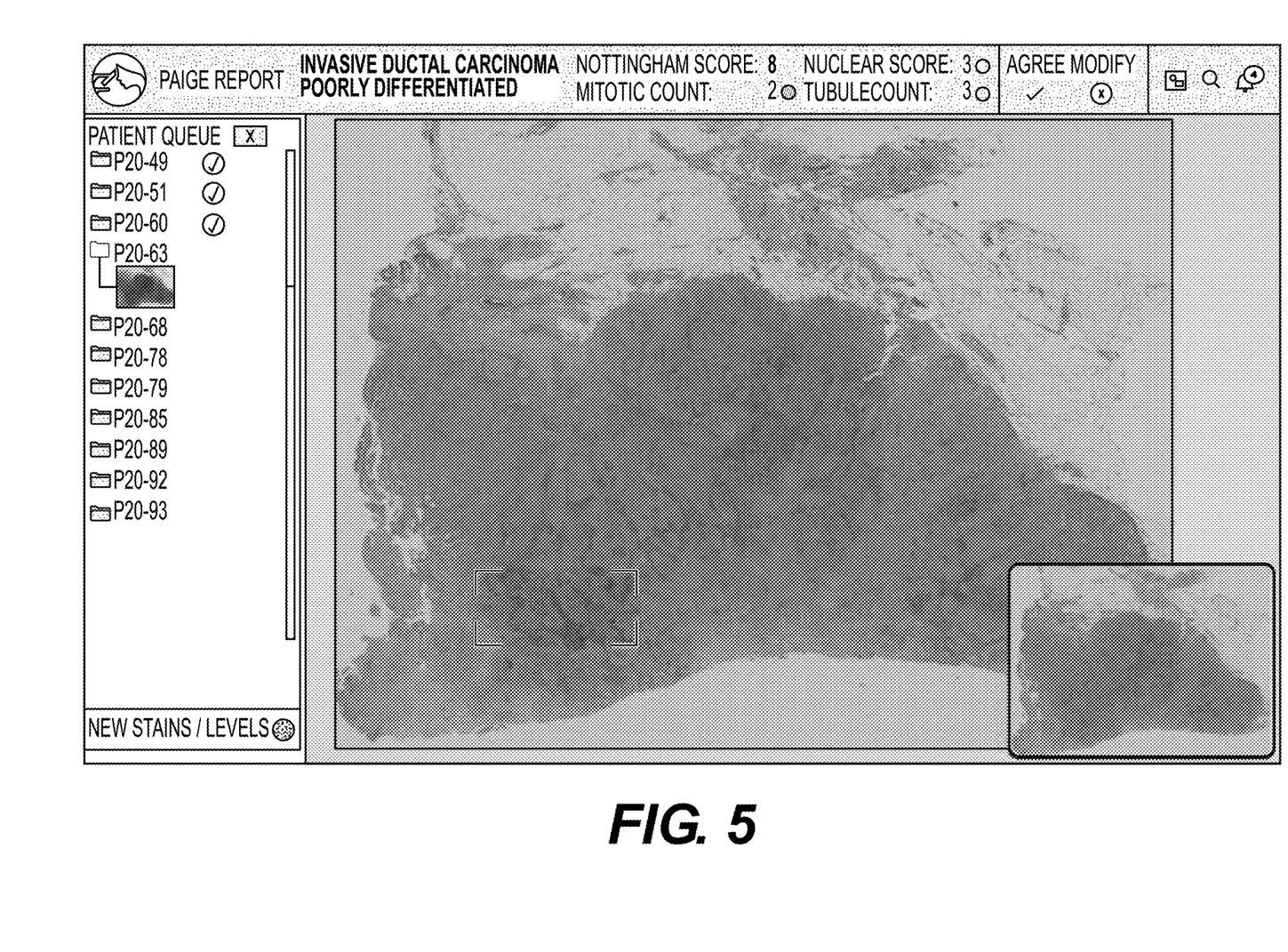
FIG. 5 is a diagram illustrating an example output of a Field of View of interest output, according to an exemplary embodiment of the present disclosure.

Exemplary Feature Identification Tool Use: An exemplary method 300 for using a feature identification tool may include one or more of the steps below. In step 302, the method may include receiving one or more digitized images of a pathology specimen (e.g., histology), related case and patient information (e.g., specimen type, case and patient ID, parts within case, gross description, etc.), and information from clinical system (e.g., assigned pathologist, specimens available for tests, etc.) into a digital storage device (e.g., hard drive, network drive, cloud storage, RAM, etc.). In step 304, predictions, recommendations, and other data may be transmitted to an electronic storage device, and a user (e.g., pathologist, oncologist, patient, etc.) may be informed that foci of interest are available. The pathologist may opt into reviewing a visualization or report. In step 306, a visualization of foci of interest may be displayed in the form of a crosshair (see FIG. 4) on one or more points of interest (with or without descriptors or other tools) and/or field of views (see FIG. 5) on one or more areas of interest (with or without descriptors or other tools). Other visual indicators may also be displayed, such as an outline of an area of interest, which may have an irregular, non-geometric or polygonal shape. The pathologist may interact with and edit the foci and/or view each region of interest in order of priority or various other types of ordering. For example, the display may be automatically modified so as to zoom in or otherwise indicate a first region of interest with the highest probability of diagnostic relevance. Upon receiving an indication such as a click from the pathologist, the display may be automatically modified to take the focus of the display to a second region of interest with the second highest probability of diagnostic relevance, and so on. The outputs and visualized regions may be logged as part of the case history within the clinical reporting system.

Exemplary Cancer Detection Tool Development: An exemplary method for developing a cancer detection tool may include one or more of the steps below. The method may include a step of receiving one or more digitized images of a pathology specimen (e.g., histology), related information (e.g., specimen type, available parts, gross description, etc.), clinical information (e.g., diagnosis), and/or patient information (e.g., demographics, gender, etc.). The method may include a step of developing a pipeline that archives processed images and prospective patient data. The method may include a step of storing data into a digital storage device (e.g., hard drive, network drive, cloud storage, RAM, etc.). The method may include a step of generating a binary output that indicates whether or not a target feature is present. The method may include a step of generating, if the feature is present (e.g., cancer present), a probability for cancer on all points of the whole slide image. The method may include a step of converting the prediction results into a form that may be visualized for and interpreted by the user (e.g., pathologist, patient, oncologist, etc.). Additionally, the results may be displayed in various effective formats depending on the user and use case (e.g., interactive, structured, templatized, static, etc.).

Exemplary Cancer Detection Tool Use: An exemplary method for using a cancer detection tool may include one or more of the steps below. The method may include a step of receiving one or more digitized images of a pathology specimen (e.g., histology), related case and patient information (e.g., specimen type, case and patient ID, parts within case, gross description, etc.), and/or information from a clinical system (e.g., assigned pathologist, specimens available for tests, etc.) into a digital storage device (e.g., hard drive, network drive, cloud storage, RAM, etc.). The method may include a step of outputting the system's predictions, recommendations, and data to an electronic storage device. A user (e.g., pathologist, oncologist, patient, etc.) may be made aware that foci of interest and/or regions of interest are available. A pathologist may opt to review the visualization and/or report. Visualization of foci of interest may be in the form of: showing one location that indicates the region with the highest statistical likelihood for harboring cancer; showing top N locations (e.g., based on user's preference) that indicate the regions with the highest statistical likelihood for harboring cancer; showing the location or locations for the region with values around the decision boundary for determining if the feature is cancer or not (e.g., three points above and three points below); and/or showing predictions on each piece of tissue on the slide (e.g., individual lymph nodes). Visualizations may be provided with descriptors (e.g., statistical likelihood, etc.) and other tools (e.g., edit, delete, move, etc.). The pathologist may interact with and edit the foci. The pathologist may be directed to each region of interest in order of priority or based on other types of ordering. The outputs and visualized regions may be logged as part of the case history within the clinical reporting system.

Exemplary Cellular Feature Tool Development: Rather than detecting a single feature, e.g., cancer, one or more embodiments may be used to predict multiple cellular features from input imagery. An exemplary method for developing a cellular feature tool may include one or more of the steps below. The method may include a step of receiving one or more digitized images of a pathology specimen (e.g., histology), related information (e.g., specimen type, available parts, gross description, etc.), clinical information (e.g., diagnosis), and/or patient information (e.g., demographics, gender, etc.). The method may include a step of developing a pipeline that archives processed images and prospective patient data. Data may be stored into a digital storage device (e.g., hard drive, network drive, cloud storage, RAM, etc.). The method may include a step of generating binary outputs that indicate whether or not each target feature is present. The method may include a step of identifying, for each feature that is present, all relevant areas where each feature is present in the whole slide image. The method may include a step of computing an overall score for each feature that may be utilized in a report. The method may include a step of converting the prediction results into a form that may be visualized for and interpreted by the user (e.g., pathologist, patient, oncologist, etc.). The results may be displayed in various effective formats depending on the user and use case (e.g., interactive, structured, templatized, static, etc.).

Exemplary Cellular Feature Tool Use: An exemplary method for using a cellular feature tool may include one or more of the steps below. The method may include a step of receiving one or more digitized images of a pathology specimen (e.g., histology), related case and patient information (e.g., specimen type, case and patient ID, parts within case, gross description, etc.), and/or information from clinical system (e.g., assigned pathologist, specimens available for tests, etc.) into a digital storage device (e.g., hard drive, network drive, cloud storage, RAM, etc.). The method may include a step of outputting the system's predictions, recommendations, and data to an electronic storage device. A user (e.g., pathologist, oncologist, patient, etc.) may be made aware that foci of interest and/or regions of interest are available. A pathologist may opt to review the visualization and/or report. Visualization of foci of interest may be in the form of: showing one location that contains the highest density of the feature of interest (e.g., mitoses, glandular/tubular differentiation, nuclear pleomorphism, basal cells, etc.) (users may select which features to show or hide); showing top N locations (e.g., based on user's preference) that indicate the regions with the highest statistical likelihood for harboring cancer; and/or showing the location or locations for the region with values around the decision boundary for determining if the feature is cancer or not (e.g., three points above and three points below). The method may include a step of showing indicators for multiple features at once or separately. Visualizations may be provided with descriptors (e.g., statistical likelihood, etc.) and other tools (e.g., edit, delete, move, etc.). The pathologist may interact with and edit the foci. The pathologist may be directed to each region of interest in order of priority or based on other types of ordering. The outputs and visualized regions may be logged as part of the case history within the clinical reporting system.

Exemplary Cancer Grade Tool Development: An exemplary method for developing a cancer grade tool may include one or more of the steps below. In this embodiment, a method is described for directing a user's attention to specific cancer grades in a whole slide image, if they are present. The method may include a step of receiving one or more digitized images of a pathology specimen (e.g., histology), related information (e.g., specimen type, available parts, gross description, etc.), clinical information (e.g., diagnosis), and patient information (e.g., demographics, gender, etc.). The method may include a step of developing a pipeline that archives processed images and prospective patient data. Data may be stored into a digital storage device (e.g., hard drive, network drive, cloud storage, RAM, etc.). The method may include a step of generating binary output that indicates whether or not a target feature is present. The method may include a step of identifying, if the feature is present (e.g., grade of cancer), all relevant areas where each feature is present in the whole slide image. The method may include a step of computing an overall score for each feature that can be utilized in a report. The method may include a step of converting the prediction results into a form that can be visualized for and interpreted by the user (e.g., pathologist, patient, oncologist, etc.). The results may be displayed in various effective formats depending on the user and use case (e.g., interactive, structured, templatized, static, etc.).

Exemplary Cancer Grade Tool Use: An exemplary method for using a cancer grade tool may include one or more of the steps below. The method may include a step of receiving one or more digitized images of a pathology specimen (e.g., histology), related case and patient information (e.g., specimen type, case and patient ID, parts within case, gross description, etc.), and information from clinical system (e.g., assigned pathologist, specimens available for tests, etc.) into a digital storage device (e.g., hard drive, network drive, cloud storage, RAM, etc.). The method may include a step of outputting the system's predictions, recommendations, and data to an electronic storage device. User (e.g., pathologist, oncologist, patient, etc.) is made aware that foci of interest and/or regions of interest are available. A pathologist may opt to review the visualization and/or report. Visualization of foci of interest may be in the form of: showing one location that contains the highest statistical likelihood of representing a particular grade of cancer (e.g., Gleason Grades 3, 4, 5 for prostate cancer, Grade 1, 2, 3 for breast cancer, Grades 1, 2, 3, 4 for lung cancer, etc.); showing top N locations (e.g., based on user's preference) that indicate the regions with the highest statistical likelihood for representing or harboring cancer grade; and/or showing the location or locations for the region with values around the decision boundary for determining if the feature is cancer or not (e.g., three points above and three points below). The method may include a step of showing indicators for multiple features at once or separately. Visualizations may be provided with descriptors (e.g., statistical likelihood, etc.) and other tools (e.g., edit, delete, move, etc.). The pathologist may interact with and edit the foci. The pathologist may be directed to each region of interest in order of priority or based on other types of ordering. The outputs and visualized regions may be logged as part of the case history within the clinical reporting system.

Exemplary Cancer Type Tool Development: An exemplary method for developing a cancer type tool may include one or more of the steps below. For some tissues, multiple forms of cancer may occur (e.g., lobular and ductal breast cancer). According to one embodiment, a user's attention may be drawn to a type of cancer present in the image. The method may include a step of receiving one or more digitized images of a pathology specimen (e.g., histology), related information (e.g., specimen type, available parts, gross description, etc.), clinical information (e.g., diagnosis), and patient information (e.g., demographics, gender, etc.). The method may include a step of developing a pipeline that archives processed images and prospective patient data. Data may be stored into a digital storage device (e.g., hard drive, network drive, cloud storage, RAM, etc.). The method may include a step of generating binary output that indicates whether or not a target feature is present. The method may include a step of identifying, if a feature is present (e.g., subtype of cancer), all relevant areas where each feature is present in the whole slide image. The method may include a step of computing an overall score for each feature that can be utilized in a report. The method may include a step of converting the prediction results into a form that may be visualized for and interpreted by the user (e.g., pathologist, patient, oncologist, etc.). The results may be displayed in various effective formats depending on the user and use case (e.g., interactive, structured, templatized, static, etc.).

Exemplary Cancer Type Tool Use: An exemplary method for using a cancer type tool may include one or more of the steps below. The method may include a step of receiving one or more digitized images of a pathology specimen (e.g., histology), related case and patient information (e.g., specimen type, case and patient ID, parts within case, gross description, etc.), and information from clinical system (e.g., assigned pathologist, specimens available for tests, etc.) into a digital storage device (e.g., hard drive, network drive, cloud storage, RAM, etc.). The method may include a step of outputting the system's predictions, recommendations, and data to an electronic storage device. A user (e.g., pathologist, oncologist, patient, etc.) may be made aware that foci of interest and/or regions of interest are available. A pathologist may opt to review the visualization and/or report. Visualization of foci of interest may be in the form of: showing one location that contains the highest statistical likelihood of representing the subtype of cancer (e.g., ductal lobular breast cancer, melanoma for skin cancer, etc.); showing top N locations (e.g., based on user's preference) that indicate the regions with the highest statistical likelihood for representing or harboring cancer subtype; showing the location or locations for the region with values around the decision boundary for determining if the feature is the cancer subtype or not (e.g., three points above and three points below). The method may include a step of showing indicators for multiple features at once or separately. Visualizations may be provided with descriptors (e.g., statistical likelihood, etc.) and other tools (e.g., edit, delete, move, etc.). The pathologist may interact with and edit the foci. The pathologist may be directed to each region of interest in order of priority or based on other types of ordering. The outputs and visualized regions may be logged as part of the case history within the clinical reporting system.

Exemplary Non-Cancerous Feature Tool Development: An exemplary method for developing a non-cancerous feature tool may include one or more of the steps below. According to one embodiment, a method includes identifying other non-cancer features, e.g., calcifications in breast tissue or identifying muscularis propria in bladder tissue samples. The method may include a step of receiving one or more digitized images of a pathology specimen (e.g., histology), related information (e.g., specimen type, available parts, gross description, etc.), clinical information (e.g., diagnosis), and patient information (e.g., demographics, gender, etc.). The method may include a step of developing a pipeline that archives processed images and prospective patient data. Data may be stored into a digital storage device (e.g., hard drive, network drive, cloud storage, RAM, etc.). The method may include a step of generating binary output that indicates whether or not a target feature is present. The method may include a step of identifying, if the feature is present (e.g., non-cancerous but suspicious features), all relevant areas where each feature is present in the whole slide image. The method may include a step of computing an overall score for each feature that may be utilized in a report. The method may include a step of converting the prediction results into a form that may be visualized for and interpreted by the user (e.g., pathologist, patient, oncologist, etc.). The results may be displayed in various effective formats depending on the user and use case (e.g., interactive, structured, templatized, static, etc.).

Exemplary Non-Cancerous Feature Tool Use: An exemplary method for using a non-cancerous feature tool may include one or more of the steps below. The method may include a step of receiving one or more digitized images of a pathology specimen (e.g., histology), related case and patient information (e.g., specimen type, case and patient ID, parts within case, gross description, etc.), and information from clinical system (e.g., assigned pathologist, specimens available for tests, etc.) into a digital storage device (e.g., hard drive, network drive, cloud storage, RAM, etc.). The method may include a step of outputting the system's predictions, recommendations, and data to an electronic storage device. A user (e.g., pathologist, oncologist, patient, etc.) may be made aware that foci of interest and/or regions of interest are available. A pathologist may opt to review the visualization and/or report. Visualization of foci of interest may be in the form of: showing one location that contains the highest statistical likelihood of representing a particular grade of cancer (e.g., fungus in derm samples, bacteria in colon samples, etc.); showing top N locations (e.g., based on user's preference) that indicate the regions with the highest statistical likelihood for representing or harboring clinical pathological features; and/or showing the location or locations for the region with values around the decision boundary for determining if the feature is suspicious or not (e.g., three points above and three points below). The method may include a step of showing indicators for multiple features at once or separately. Visualizations may be provided with descriptors (e.g., statistical likelihood, etc.) and other tools (e.g., edit, delete, move, etc.). The pathologist may interact with and edit the foci. The pathologist may be directed to each region of interest in order of priority or based on other types of ordering. The outputs and visualized regions may be logged as part of the case history within the clinical reporting system.

Exemplary Invasion Tool Development: In cancer pathology, one of the tasks of a pathologist is determining if invasion is present. An exemplary method for developing an invasion tool may include one or more of the steps below. The method may include a step of receiving one or more digitized images of a pathology specimen (e.g., histology), related information (e.g., specimen type, available parts, gross description, etc.), clinical information (e.g., diagnosis), and patient information (e.g., demographics, gender, etc.). The method may include a step of developing a pipeline that archives processed images and prospective patient data. Data may be stored into a digital storage device (e.g., hard drive, network drive, cloud storage, RAM, etc.). The method may include a step of generating binary output that indicates whether or not a target feature is present. The method may include a step of identifying, if the feature is present (e.g., invasion of cancer), all relevant areas where each feature is present in the whole slide image. The method may include a step of computing an overall score for each feature that may be utilized in a report. The method may include a step of converting the prediction results into a form that may be visualized for and interpreted by the user (e.g., pathologist, patient, oncologist, etc.). The results may be displayed in various effective formats depending on the user and use case (e.g., interactive, structured, templatized, static, etc.).

Exemplary Invasion Tool use: An exemplary method for using an invasion tool may include one or more of the steps below. The method may include a step of receiving one or more digitized images of a pathology specimen (e.g., histology), related case and patient information (e.g., specimen type, case and patient ID, parts within case, gross description, etc.), and information from clinical system (e.g., assigned pathologist, specimens available for tests, etc.) into a digital storage device (e.g., hard drive, network drive, cloud storage, RAM, etc.). The method may include a step of outputting the system's predictions, recommendations, and data to an electronic storage device. A user (e.g., pathologist, oncologist, patient, etc.) may be made aware that foci of interest and/or regions of interest are available. A pathologist may opt to review the visualization and/or report. Visualization of foci of interest may be in the form of: showing one location that contains the highest statistical likelihood of representing evidence of invasive cancer (e.g., microinvasion in breast cancer, muscularis propria invasion in bladder cancer, perineural invasion in prostate cancer, etc.); showing top N locations (e.g., based on user's preference) that indicate the regions with the highest statistical likelihood for representing or harboring evidence of cancer invasion; and/or showing the location or locations for the region with values around the decision boundary for determining if the feature is invasive or not (e.g., three points above and three points below). The method may include a step of showing indicators for multiple features at once or separately. Visualizations may be provided with descriptors (e.g., statistical likelihood, etc.) and other tools (e.g., edit, delete, move, etc.). The pathologist may interact with and edit the foci. The pathologist may be directed to each region of interest in order of priority or based on other types of ordering. The outputs and visualized regions may be logged as part of the case history within the clinical reporting system.

According to one or more embodiments, a limited number of regions or field of views on a whole slide image may be displayed to the pathologist and those selected regions may be sufficient to complete a specific task in the diagnostic process (e.g., cancer detection, grading, triaging, etc.).

One or more embodiments may be implemented within a clinical workflow at the hospital, lab, medical center as (1) Web application (cloud-based or on-premises); (2) Mobile application; (3) Interactive report; (4) Static report; and/or (5) Dashboard.

To improve ease of use, one or more embodiments may be implemented such that the area(s) with salient information may be organized into a report with overview information, or an interactive review/edit may be facilitated by the pathologist during review of the whole slide image.

One or more embodiments may be implemented such that multiple features may be visualized on a single whole slide image.

The technical workflow according to one or more embodiments may be as follows: a digitized whole slide image may be created and some or all metadata may be available from hospital and hardware databases; image and corresponding data may be passed into an artificial intelligence (AI)-based system and outputs may be generated; and/or some of the outputs may be fed into a system that generates and displays the visualization (e.g., one or multiple points or regions) to the pathologist based on the query of interest (e.g., cancer, nuclear features, cell count, etc.).

Additionally, one or more embodiments of the present disclosure may be used for pre-screening (i.e., before a pathologist reviews an image) and/or after a diagnosis has been rendered (e.g., quality assurance).

Figure 6:
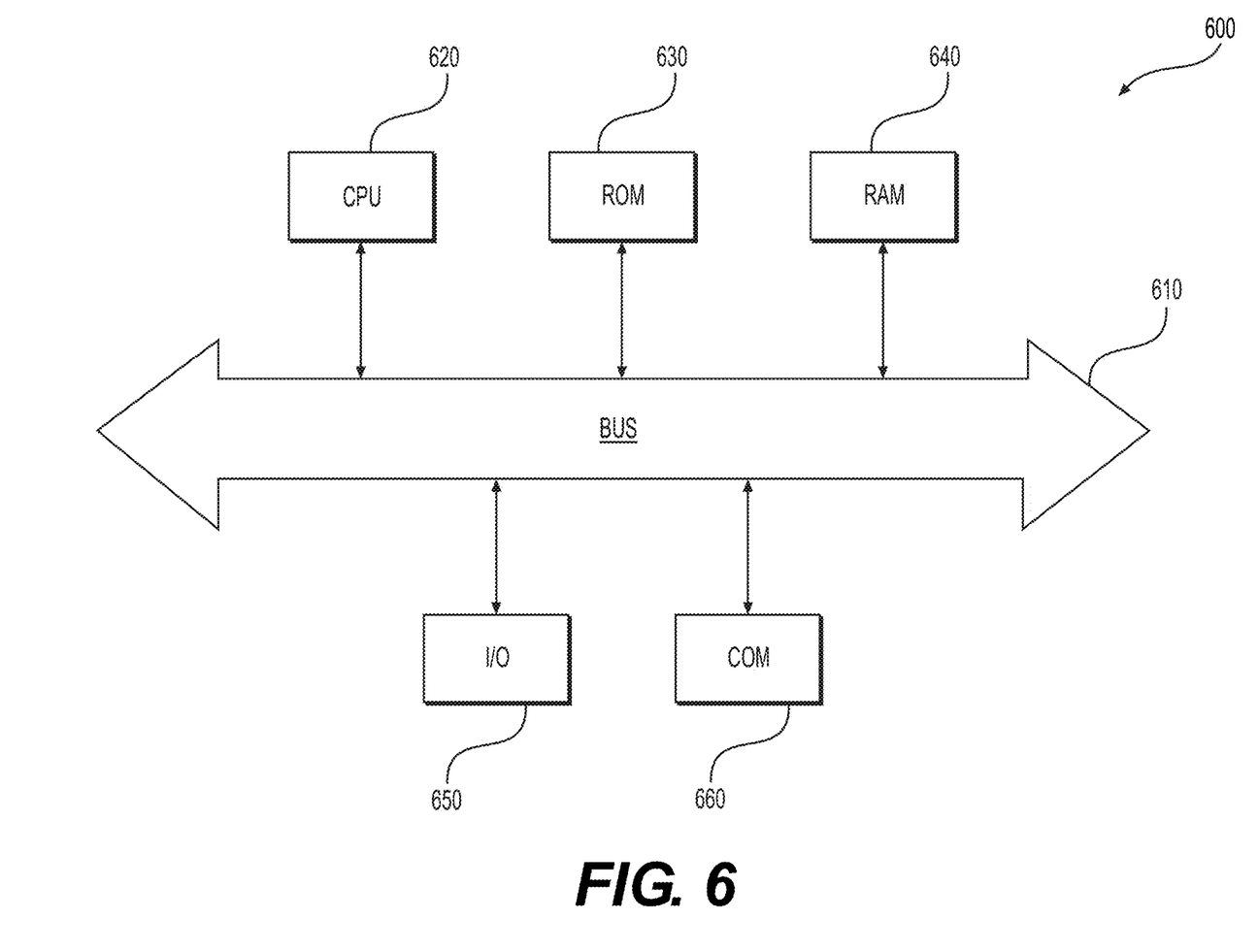
FIG. 6 depicts an example system that may execute techniques presented herein.

As shown in FIG. 6, device 600 may include a central processing unit (CPU) 620. CPU 620 may be any type of processor device including, for example, any type of special purpose or a general-purpose microprocessor device. As will be appreciated by persons skilled in the relevant art, CPU 620 also may be a single processor in a multi-core/multi-processor system, such system operating alone, or in a cluster of computing devices operating in a cluster or server farm. CPU 620 may be connected to a data communication infrastructure 610, for example, a bus, message queue, network, or multi-core message-passing scheme.

Device 600 also may include a main memory 640, for example, random access memory (RAM), and also may include a secondary memory 630. Secondary memory 630, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 630 may include other similar means for allowing computer programs or other instructions to be loaded into device 600.

Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 600.

Device 600 also may include a communications interface ("COM") 660. Communications interface 660 allows software and data to be transferred between device 600 and external devices. Communications interface 660 may include a modem, a network interface (such as an Ethernet card), a communications port, a PCMCIA slot and card, or the like. Software and data transferred via communications interface 660 may be in the form of signals, which may be electronic, electromagnetic, optical, or other signals capable of being received by communications interface 660. These signals may be provided to communications interface 660 via a communications path of device 600, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 600 also may include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for identifying a diagnostic feature of a digitized pathology image, the method comprising:

receiving one or more digitized images of a pathology specimen, and medical metadata comprising image metadata, specimen metadata, clinical information, and patient information;

applying a machine learning model to generate one or more predictions based on a presence of one or more pathological conditions in the one or more digitized images, the one or more predictions comprising a binary output to indicate a plurality of relevant diagnostic features based on medical metadata, the machine learning model having been developed using an archive of processed images and prospective patient data comprising at least one of a tissue type, a specimen type, and a stain type;

generating, by the machine learning model, at least one relevant diagnostic feature of the relevant diagnostic features for output to a display, the at least one relevant diagnostic feature being based on the presence of a region having the one or more pathological conditions beyond a statistical likelihood, the pathological conditions comprising biomarkers, cancer, grade of cancer, non-cancerous features, nuclear features, and/or cell count; and providing, by the machine learning model, the at least one relevant diagnostic feature to the display as a region of interest indicated by at least one of an outline comprising a non-geometric shape.

2. The computer-implemented method of claim 1, wherein the generating at least one relevant diagnostic feature further comprises:

determining a probability of diagnostic relevance for each of the plurality of relevant diagnostic features; and determining a highest probability among the plurality of relevant diagnostic features for output to the display.

3. The computer-implemented method of claim 1, wherein the generating at least one relevant diagnostic feature further comprises:

determining at least one probability of diagnostic relevance that exceeds a predetermined value among the plurality of relevant diagnostic features for output to the display.

4. The computer-implemented method of claim 1, wherein the generating at least one relevant diagnostic feature further comprises:

determining a predetermined number of highest probabilities of diagnostic relevance among the plurality of relevant diagnostic features for output to the display.

5. The computer-implemented method of claim 1, further comprising:

determining a ranking of probabilities of diagnostic relevance of each of the plurality of relevant diagnostic features;

automatically focusing the display on each of the relevant diagnostic features in order based upon the determining of the ranking of probabilities of diagnostic relevance; and receiving a user input to modify a focus of the display from a first relevant diagnostic feature to a second relevant diagnostic feature.

6. The computer-implemented method of claim 1, wherein at least one field of interest is indicated on a digitized pathology image.

7. The computer-implemented method of claim 1, wherein the method further comprises storing a collection of data into a digital storage device.

8. The computer-implemented method of claim 1, wherein the method further comprises generating a probability for biomarkers, cancer, and/or histological features on all points of a whole slide image.

9. The computer-implemented method of claim 1, wherein the method further comprises identifying a set of relevant areas where the one or more pathological conditions is present in a whole slide image.

10. The computer-implemented method of claim 9, wherein the method further comprises computing an overall score for each pathological condition.

11. A system for identifying a diagnostic feature of a digitized pathology image, the system comprising:
at least one memory storing instructions; and
at least one processor configured to execute the instructions to perform operations comprising:
receiving one or more digitized images of a pathology specimen, and medical metadata comprising at least one of image metadata, specimen metadata, clinical information and/or patient information;
applying a machine learning model to generate one or more predictions based on a presence of one or more pathological conditions in the one or more digitized images, the one or more predictions comprising a binary output to indicate a plurality of relevant diagnostic features based on medical metadata, the machine learning model having been developed using an archive of processed images and prospective patient data;
generating, by the machine learning model, at least one relevant diagnostic feature of the relevant diagnostic features for output to a display, the at least one relevant diagnostic feature being based on the presence of a region having the one or more pathological conditions beyond a statistical likelihood, the pathological conditions comprising biomarkers, cancer, grade of cancer, non-cancerous features, nuclear features, and/or cell count; and
providing, by the machine learning model, the at least one relevant diagnostic feature to the display as a region of interest indicated by at least one of an outline comprising a non-geometric shape.

12. The system of claim 11, wherein the generating at least one relevant diagnostic feature further comprises:
determining a probability of diagnostic relevance for each of the plurality of relevant diagnostic features; and
determining a highest probability among the plurality of relevant diagnostic features for output to the display.

13. The system of claim 11, wherein the generating of at least one relevant diagnostic feature further comprises:
determining at least one probability of diagnostic relevance that exceeds a predetermined value among the plurality of relevant diagnostic features for output to the display.

14. The system of claim 11, wherein the generating at least one relevant feature further comprises:
determining a predetermined number of highest probabilities of diagnostic relevance among the plurality of relevant diagnostic features for output to the display.

15. The system of claim 11, further comprising:
determining a ranking of probabilities of diagnostic relevance of each of the plurality of relevant diagnostic features;
automatically focusing the display on each of the relevant diagnostic features in order based upon the determining of the ranking of probabilities of diagnostic relevance; and
receiving a user input to modify a focus of the display from a first relevant diagnostic feature to a second relevant diagnostic feature.

16. The system of claim 11, wherein at least one field of interest is indicated on a digitized pathology image.

17. A non-transitory computer-readable medium storing instructions that, when executed by a processor to perform a method for identifying a diagnostic feature of a digitized pathology image, the method comprising:
at least one memory storing instructions; and
at least one processor configured to execute the instructions to perform operations comprising:
receiving one or more digitized images of a pathology specimen, and medical metadata comprising at least one of image metadata, specimen metadata, clinical information and/or patient information;
applying a machine learning model to generate one or more predictions based on a presence of one or more pathological conditions in the one or more digitized images, the one or more predictions comprising a binary output to indicate a plurality of relevant diagnostic features based on medical metadata, the machine learning model having been developed using an archive of processed images and prospective patient data;
generating by the machine learning model, at least one relevant diagnostic feature of the relevant diagnostic features for output to a display, the at least one relevant diagnostic feature being based on the presence of a region having the one or more pathological conditions beyond a statistical likelihood, the pathological conditions comprising biomarkers, cancer, grade of cancer, non-cancerous features, nuclear features, and/or cell count; and
providing, by the machine learning model, the at least one relevant diagnostic feature to the display as a region of interest indicated by at least one of an outline comprising a non-geometric shape.

* * * * *